United States Patent [19]
Martinez

[11] Patent Number: 5,960,231
[45] Date of Patent: Sep. 28, 1999

[54] VARIABLE THICKNESS CONCENTRATE SENSE WINDOW

[75] Inventor: José Natividad Martinez, San Jose, Calif.

[73] Assignee: Xerox Corporation, Stamford, Conn.

[21] Appl. No.: 09/185,193

[22] Filed: Nov. 3, 1998

[51] Int. Cl.$^6$ ................................................. G03G 15/10
[52] U.S. Cl. .......................... 399/30; 399/64; 399/247; 430/117; 356/442
[58] Field of Search .................. 399/30, 27, 28, 399/64, 233, 237, 247; 430/117, 119; 356/434, 436, 441, 442

[56] References Cited

U.S. PATENT DOCUMENTS

| | | |
|---|---|---|
| 3,999,119 | 12/1976 | Bares . |
| 4,166,702 | 9/1979 | Okamoto et al. ......................... 399/57 |
| 4,222,497 | 9/1980 | Lloyd et al. ........................ 222/DIG. 1 |
| 4,660,152 | 4/1987 | Downing et al. . |
| 4,671,309 | 6/1987 | Iemura et al. ............................. 399/57 |
| 4,981,362 | 1/1991 | deJong et al. . |
| 5,053,822 | 10/1991 | Butler . |
| 5,081,491 | 1/1992 | Lux et al. . |
| 5,319,421 | 6/1994 | West . |
| 5,369,476 | 11/1994 | Bowers et al. . |
| 5,410,388 | 4/1995 | Pacer et al. . |
| 5,574,539 | 11/1996 | Wong . |
| 5,581,335 | 12/1996 | Borton et al. . |
| 5,678,126 | 10/1997 | Rathbun .................................... 399/30 |

OTHER PUBLICATIONS

Patent abstracts of Japan, vol. 95, No. 3 for JP–A–0763678, Mar. 10, 1995.

*Primary Examiner*—R. L. Moses
*Attorney, Agent, or Firm*—Fay, Sharpe, Beall, Fagan, Minnich & Mckee, LLP

[57] ABSTRACT

A concentrate sense window which defines a variable thickness flow path area is provided for sensing the concentration levels of inks having varying levels of luminance. Sensor window panels are configured in relationship to each other such that an area defined therebetween varies from a first area to a second area. An emitter/detector pair are located on opposite sides of the sensor window. The emitter transmits a signal through the sensor area and at least part of the signal is sensed by the detector. The emitter/detector pair are designed so as to be movable along the surface of the sensor window whereby ink of varying illuminance may be sensed without the need of separate windows or multiple emitter/detector pairs.

18 Claims, 4 Drawing Sheets

BLACK WINDOW

YELLOW WINDOW

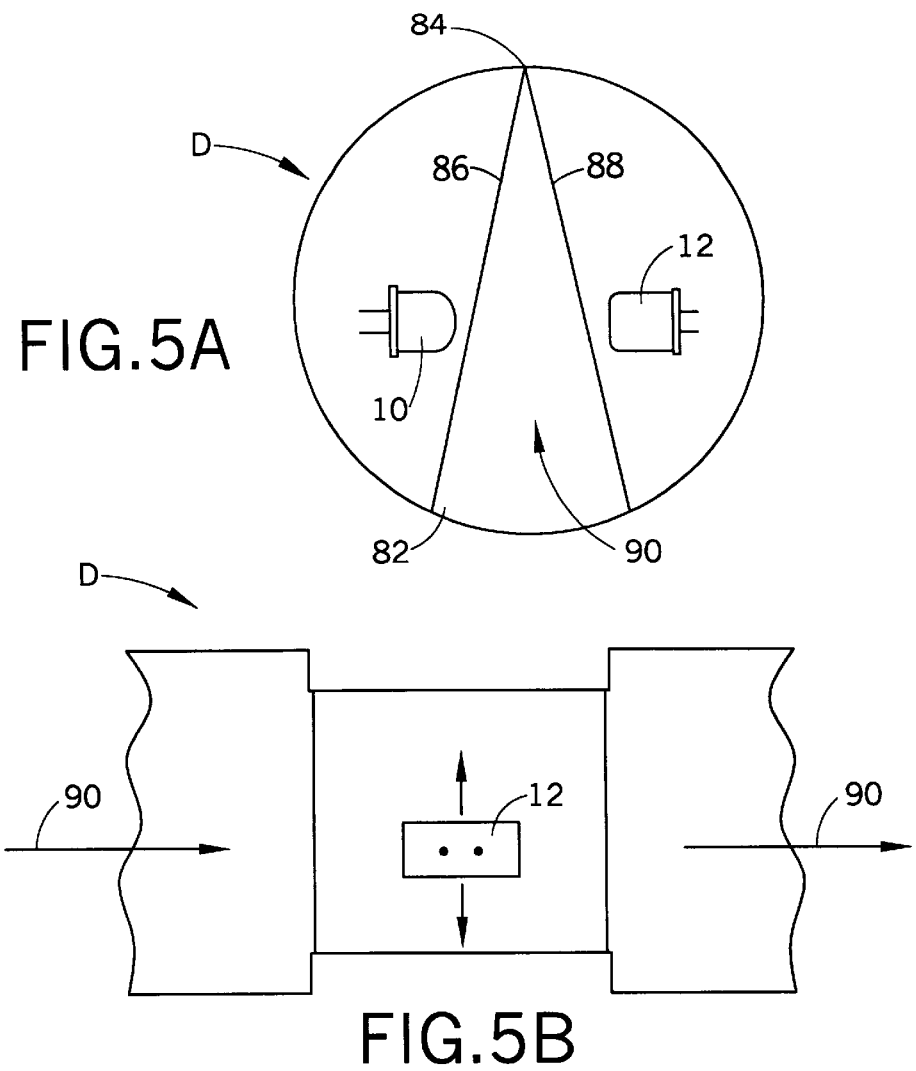
FIG.5A
FIG.5B
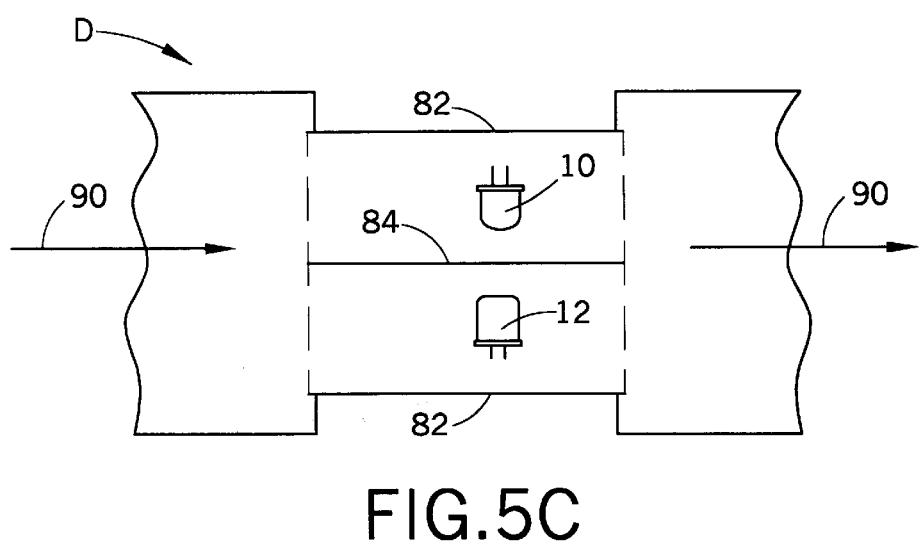
FIG.5C

VARIABLE THICKNESS CONCENTRATE SENSE WINDOW

BACKGROUND OF THE INVENTION

The present invention is directed to a device and method for sensing and monitoring the concentration level of a material carried in a body of fluid. More particularly, the invention relates to a device and method which senses and monitors the toner concentration within a liquid solution used in connection with an electrographic printing machine.

Electrographic reproduction includes forming an electrostatic latent image upon a recording medium and subsequently making the latent image visible. The recording medium is usually provided in web form, and has a dielectric and a conductive surface. The medium may be a coated paper, a polyester based transparent film, or other suitable material on which an electrostatic latent image is formed by means of a plurality of writing electrodes physically positioned on one side to electrically address the dielectric surface as the medium travels through a recording station. Opposite the dielectric surface of the recording medium there is a conductive surface which is selectively grounded. When the potential difference between the conductive surface and the recording elements is raised above a threshold level, on the order of several hundred volts, an electrostatic charge is deposited on the dielectric surface of the recording medium as the medium passes by the recording station.

Subsequently, the latent image is made visible at a development station during a development step by applying liquid or dry toner to the recording medium. The recording medium is contacted by a thin film of developer material out of which the toner particles are electrostatically attracted to the regions of electrostatic charge on the medium. These toner particles often are suspended in a liquid solution at a preferred concentration. As more images are developed, the particles suspended in the liquid become depleted causing the concentration of the particles in the liquid to be reduced. Therefore, as will become apparent, it is important to monitor the depletion of these particles as the concentration of the liquid changes, and to compensate for such depletions as they occur.

Electrographic machines, such as electrostatic plotters are available as monochrome machines, including a single recording station and a single development station dispensing a single color toner, usually black. Also, electrostatic color plotters are available which produce full color plots by the sequential overlaying of a series of separate color images (yellow, cyan, magenta and black) to produce a full spectrum of colors.

There are three basic approaches to color separation imaging. In the first, a series of images are formed sequentially each by means of a dedicated recording head and development station. In the second, a single recording head forms each color separation image on the recording medium which is then advanced past one of several development stations. Then, the recording medium is returned to the recording head for receiving the next color separation image and is advanced to the next development station. This process of advancing and returning the recording medium through the apparatus minimizes the number of recording heads and obviates the need for their critical alignment with respect to one another.

The third approach to color separation imaging uses a single recording head to form each color separation image on the recording medium, as in the second approach described above, however only one toner fountain is used for development whereby all toners pass through the same fountain which is purged between colors.

Each of the foregoing systems need to compensate for changes in toner concentration. In liquid toner electrostatic plotters, toner concentration is commonly measured optically. The liquid toner is pumped between two closely spaced, parallel, clear windows, forming a thin layer through which light is passed by an emitter, such as an LED. Toner concentration is determined to be proportional to the amount of light registered at an optical sensor. For example, the higher the number of particles in a fluid the more the light passing to the sensor is blocked. A full description of such a system is detailed in U.S. Pat. No. 4,222,497 to Lloyd et al. which is assigned to a common assignee and hereby incorporated by reference. Various other systems using this approach are described in U.S. Pat. Nos.: 5,319,421; 4,981,362; 4,660,152; 4,166,702; 4,119,989; 3,807,872; 3,712,203; 3,698,356; 3,677,222; and 3,354,802. Typically, color electrographic systems have four such windows, one for each color (e.g. black, cyan, magenta, yellow). U.S. Pat. No. 5,319,421 to West describes a concentrate sensor which has two different sized windowing areas used to compensate for the difference in the optical properties of different color toner solutions. West also discloses self-calibration method for measurement of toner concentrate.

The accuracy of concentration measurement is highly sensitive to the thickness of the toner layer, i.e. the "window thickness", as well as variations in the optical properties of the toner being measured. This requires very tight tolerances on the window (e.g. 20±1 mil) which, realistically, can only be met by sorting parts. A common technique is to calibrate a machine during its manufacture to compensate for the initial properties of the elements being used. This type of calibration process does not, however, take into account element properties that change or degrade over time. In addition, any improvements in toner formulation which affect optical properties cannot be easily implemented.

As technology moves forward and new toners are developed, existing concentration sensors are becoming ineffective in the sensing of color extremes, i.e. black and yellow. For example, a situation is developing where, due to the tight tolerances that are required, and the differences in the black toner solutions, it is difficult to construct a window thin enough to accurately measure these solutions.

To compensate for the deficiencies in concentrate sensors, manufacturers are turning to higher-capability emitters and detectors. These devices are of course more costly which results in a more expensive machine. Another manner of compensating for the deficiencies described above, is to include a circuit which amplifies the detected signal. However, a drawback with such a solution is the amplification of noise such as ambient light and reflection noise. These undesirable amplifications are significant enough to effect readings.

Another drawback with existing concentrate sensors is the need for multiple sensor windows for each of the colors (e.g. black, cyan, magenta, yellow) or the requirement of additional emitters and detectors and a complex multi-level window area such as necessary in the patent to West.

Still a further drawback has to do with calibration of the concentrate sensor. Particularly, while it was noted that calibrations could be performed during machine manufacture, this does not take into account the calibrations necessary or desirable when new toners are added to the machine or the effects of time on components. In these existing machines, it is often necessary for a technician to manually "tweak" the amount of light going through the emitter. While West does describe a self-calibration technique, the implementation of it, is complex requiring use of CPU time and the generation of a variety of look-up tables.

Another drawback with existing concentrate sensors is their inability to be easily implemented within machines having different characteristics, such as between a single toner machine to one with four color toners. This is a matter of significant concern since machines having five and six toners are now under development. Under the present technology such machines would therefore require additional sensor windows or windows of greater size to be implemented, thereby raising the cost and complexity of these machines.

It has been determined to be advantageous to have a variable concentrate sensor with a variable sensor window and emitter and detector which can measure the density of a range of colors without the requirement of increasing the window size and/or requiring additional sensor windows and/or associated emitters and detectors.

It has also been considered valuable to provide a variable concentrate sensor which can measure toners, such as different types of black toner that can have widely varying characteristics. It is also considered valuable to have a variable concentrate sensor which eliminates the complexity of recalibration when new toner is added to a machine. A concentrate sensor of such construction is also considered valuable for calibration as it eliminates the need of a technician and/or the acquisition of information and operations needed to generate look-up tables.

Still another desirable aspect of a variable concentrate sensor is one which allows a larger mechanical variance in the construction of the sensor windows, thereby decreasing the number of non-usable manufactured parts.

SUMMARY OF THE INVENTION

In accordance with the present invention, provided is a variable concentrate sensor for sensing material carried in a fluid medium. The variable concentrate sensor includes a concentrate sense window with a varying thickness which includes a sensor system having an emitter and detector arranged to move along outer surfaces of the sense window, dependent upon the translucence of the fluid medium. It noted that a fluid medium with a high translucence will allow a greater amount of light to pass therethrough, than a fluid medium with low translucence.

With attention to a more limited aspect of the invention, the variable thickness concentrate sense window has a first opening larger than a second opening whereby fluid having high translucence is measured near the first opening and a fluid having low translucence is measured near the second opening.

With attention to still another aspect of the present invention, the variable sense window is in the form of a triangle whereby a section of a first side and a second side of the triangle are pinched together.

It is therefore an object of the present invention to provide an improved concentrate sensor which has the capability of measuring multiple colors without a need of increasing the size or complexity of the sense window, or adding additional windows to the system.

It is a further object of the present invention that the variable thickness concentrate sense window be formed in the arrangement of a triangle, wherein the upper edges of the glass window which are pinched together provide a minimal area in which toner having minimal translucence is sensed.

It is a further object of the present invention to provide an infinitely variable concentrate sensor wherein an emitter and detector traverse outer portions of a variable thickness concentrate sense window.

These together with other objects of the invention, along with various features of novelty which characterize the invention, are pointed out with particularly in the claims attached to and forming a part of this disclosure. For a better understanding of the invention, its operating advantages and the specific objects obtained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the attached drawings wherein:

FIG. 5A is an end view of a second embodiment for the concentrate sensor of the present invention;

FIG. 5B is a side view of the sensor of FIG. 5A;

FIG. 5C is a top view of the sensor of FIG. 5A.

DETAILED DESCRIPTION OF THE PREFERRED EMBODIMENTS

Figure 1A:
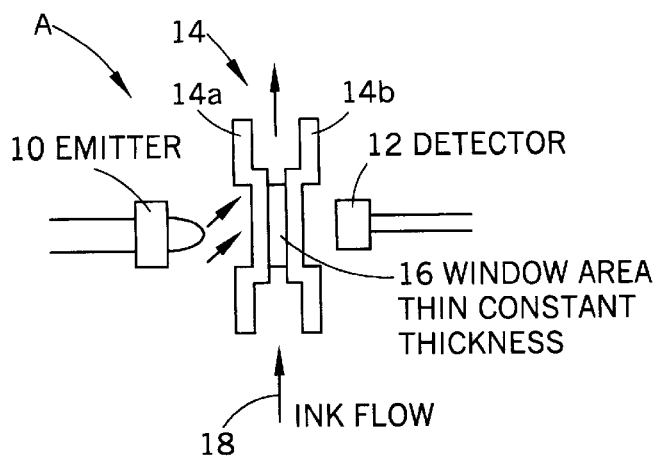
FIGS. 1A-1B illustrate constant thickness windows for a black concentrate sense window and a yellow concentrate sense window.
Figure 1B:
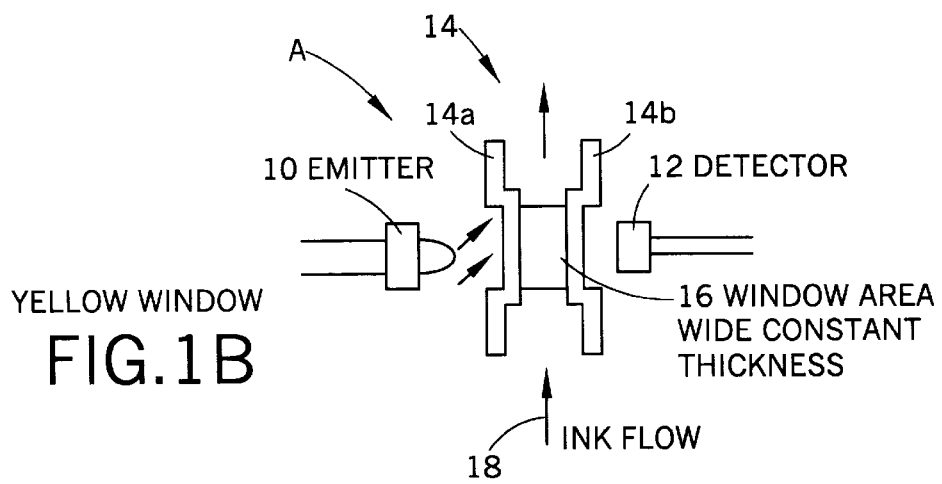

Referring to FIGS. 1A and 1B, concentrate sensors A and B are shown respectively. Each concentrate sensor A and B includes an emitter 10 and detector 12. Positioned between these elements is a sensor window 14, comprised of a first window surface 14a and a second window surface 14b. Sensor window 14 of each device is of a constant thickness across the window area 16 which provides a liquid toner path 18 for liquid toner being monitored. As can be seen by viewing FIGS. 1A and 1B, in existing systems the thickness of window 14 is calibrated for a particular color of toner. For example, window area 16 of FIG. 1A is smaller than the window area of FIG. 1B.

As described in the foregoing, thickness differences are necessary due to the differences in translucence of toner, such as black toner versus yellow toner. Because of the constant window thickness in existing devices, it is necessary to have multiple windows of varying thicknesses in machines which are color printers. Labor-intensive methods are used to calibrate each window for its specific toner station. Due to the constant window thickness of existing concentrate sensors, a concentrate sensor system needs to be redesigned each time consistently changing toner concentrations exceed the system's fixed design parameters. It has been determined that existing concentrate sense systems are reaching their maximum efficiency. It has now become necessary to create special software and circuitry to sense the extreme concentrations, i.e. black and yellow toner. Additionally, more sensitive, and therefore expensive, detectors and emitters are needed in order to meet the requirements of these extreme concentrations. Further, calibration of the concentrate sense system needs to be done by a knowledgeable technician.

Figure 2:
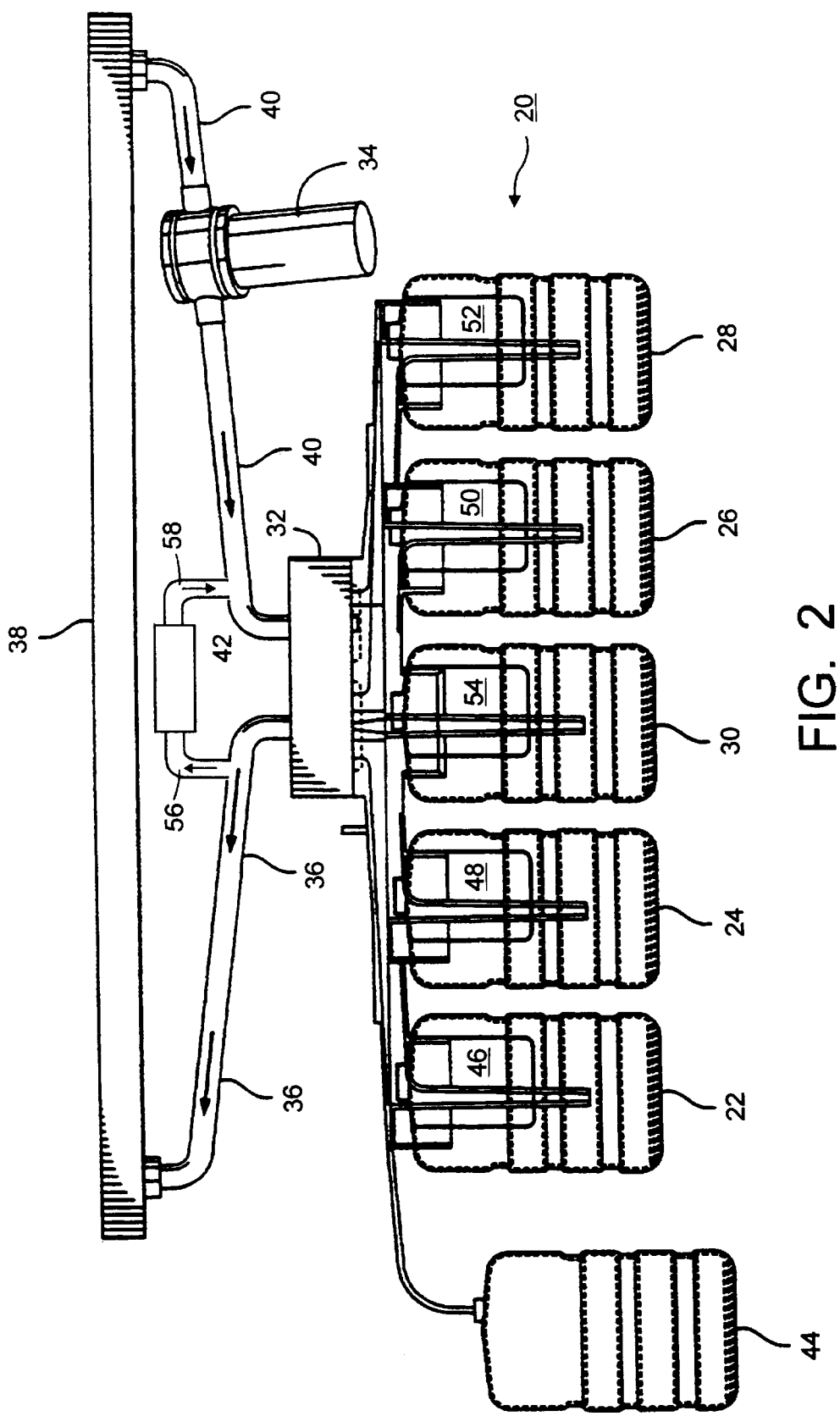
FIG. 2 is a schematic front view of a toning system of an electrographic plotting apparatus in which the present invention is implemented.

For an understanding of the operation of concentrate sensors, such as A & B of FIGS. 1A and 1B, in an overall system, reference is made to FIG. 2 which is a front view of toning system 20 of a color electrostatic plotter which uses liquid toner. As will be seen, each color toner circulates through a common plumbing of toner system 20 as shown, and the common plumbing is flushed with a clear dispersant such as ISOPAR (which is a registered trademark of Exxon Corporation) between color passes.

Toner system 20 houses toner solution bottles 22, 24, 26, 28, and clear dispersant bottle 30. During development of an electrostatic image onto a medium, each toner bottle is connected in turn to the common plumbing by valve 32. Due to the action of pump 34, the toner solution, for example from bottle 28, is drawn through valve 32 and tube 36 in the direction indicated by the arrow, and into fountain 38 where the toner solution comes in contact with the print medium. Excess toner solution is then returned to bottle 28 through tube 40 and valve 32. As will be discussed later, the toner solution passing through tube 36 is measured by concentrate window sensor 42.

Next, valve 32 connects clear dispersant bottle 30 to the common plumbing, allowing a clear dispersant such as ISOPAR® to be used. Dispersant from bottle 30 flushes all of the common plumbing of system 20, including valve 32, tubes 40, 36, fountain 38 and concentrate sensor 42, and the dirty dispersant is directed to bottle 44. The process of shifting valve 32, toning and flushing the plumbing is repeated for each color pass of the plotting operation.

Each time a plot is made and toner solution is used, the concentration of solids in toner solution bottles 22, 24, 26, 28 becomes depleted. Image quality depends on maintaining the correct concentration of solids in the toner solution. In the present invention, measuring toner concentration is accomplished by concentrate sensor 42. Using information from concentrate sensor 42, high solid concentrate is added to the toner solution as required. As depicted in FIG. 2, each toner solution bottle has an associated concentrate solution bottle 46, 48, 50, 52 respectively. Concentrate from bottles 46, 48, 50, 52 is added to the toner solutions of bottles 22, 24, 26, 28 to bring the toner solution in these bottles back to a desired concentration. In a similar manner, when the clear dispersant in bottle 30 becomes depleted, new dispersant from bottle 54 is added to the dispersant in bottle 30.

Concentrate sensor 42 is configured to accept small amounts of the liquid toner through input line 56, which is sensed by concentrate sensor 42 and then passed to bottle 44 via return line 56. In this embodiment, the toner solution concentration is to be measured optically, although the concepts of the present invention may also be applicable to acoustic measurements.

Figure 3:
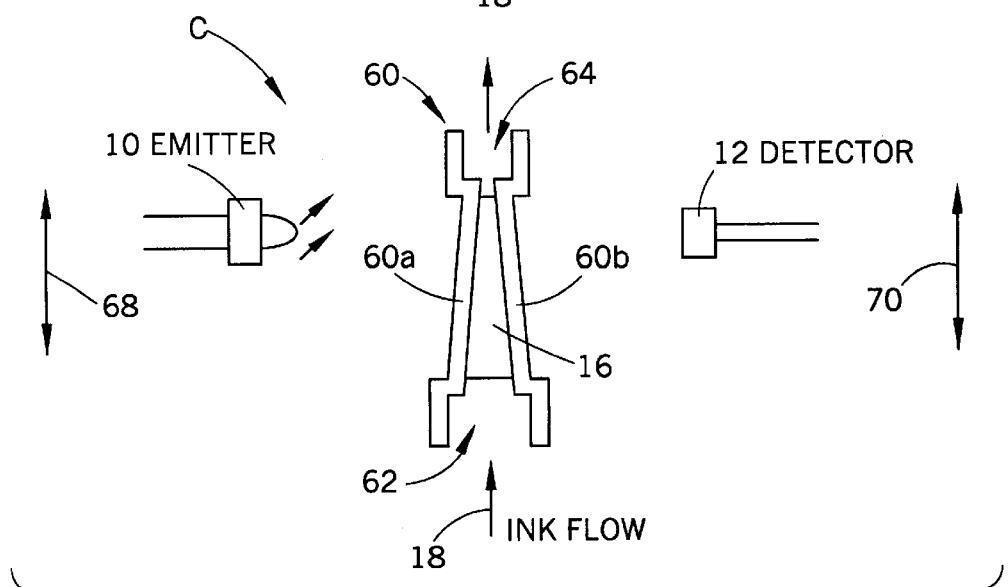
FIG. 3 describes a concentrate sensor using a variable thickness concentrate sense window according to the present invention.

Turning attention to FIG. 3, a concentrate sensor C according to the teachings of the present invention which can be incorporated in a location as concentrate sensor 42, is illustrated. Concentrate sensor C includes emitter 10 and detector 12 located on each side of a variable concentrate sense window 60, including a first window surface 60a and a second window surface 60b. As disclosed in this figure, concentrate sense window 60 is a variable thickness concentrate sense window with varying window area 16. The arrangement has a first opening 62 having a significantly larger diameter than a second opening 64. Thus, an ink path 66 is provided through opening 62 which then narrows the fluid flow down to opening 64. As further disclosed, emitter 10 and detector 12 are each constructed to be movable along window area 16 as shown by arrows 68 and 70. By this arrangement, when variable sense window 60 is used to detect a dark toner within ink path 66, the emitter 10, detector 12 pair will be located towards second opening 64 of variable sense window 60. When the toner is a more translucent color, such as yellow, the emitter 10, detector 12 pair are moved to a location towards opening 62. Because of the variability of concentrate sensor C, toners having a wide difference in translucence, and toners with changing characteristics can be monitored with the same concentrate sensor C.

Variable sense window 60 can also be manufactured to less precise mechanical tolerances than previous sense windows, thereby improving the build-yield efficiency. Specifically, in the present invention, the need for calibration of the emitter and detector can be accomplished by moving emitter 10 and detector 12 anywhere along the length of variable sense window 60. Additionally, calibration during production of these windows is eliminated due to the infinite amount of variability. The increased variability of concentrate sensor C also reduces the need for special hardware and software required in previous systems. Less expensive emitters and detectors can be used. Calibration of the ink system can now be more particularly automated and there is no need for a specialized technician to calibrate the system when installing a new set of toner in the machine.

Figure 4A:
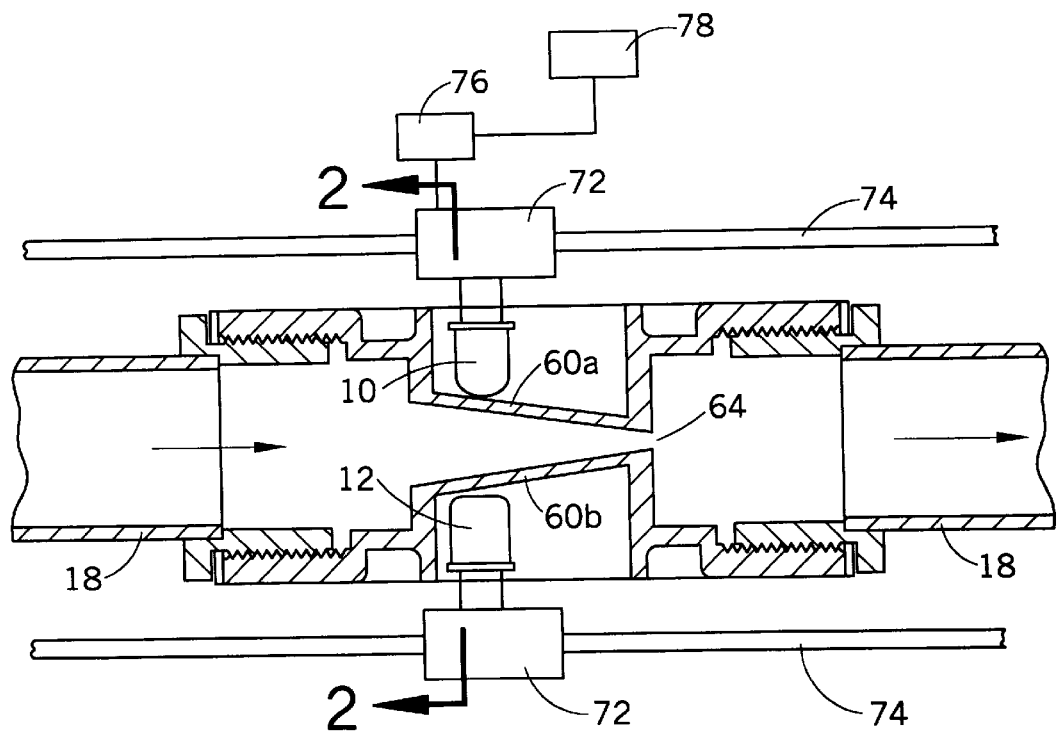
FIG. 4A illustrates the sensor of FIG. 3 incorporated into the system of FIG. 2.
Figure 4B:
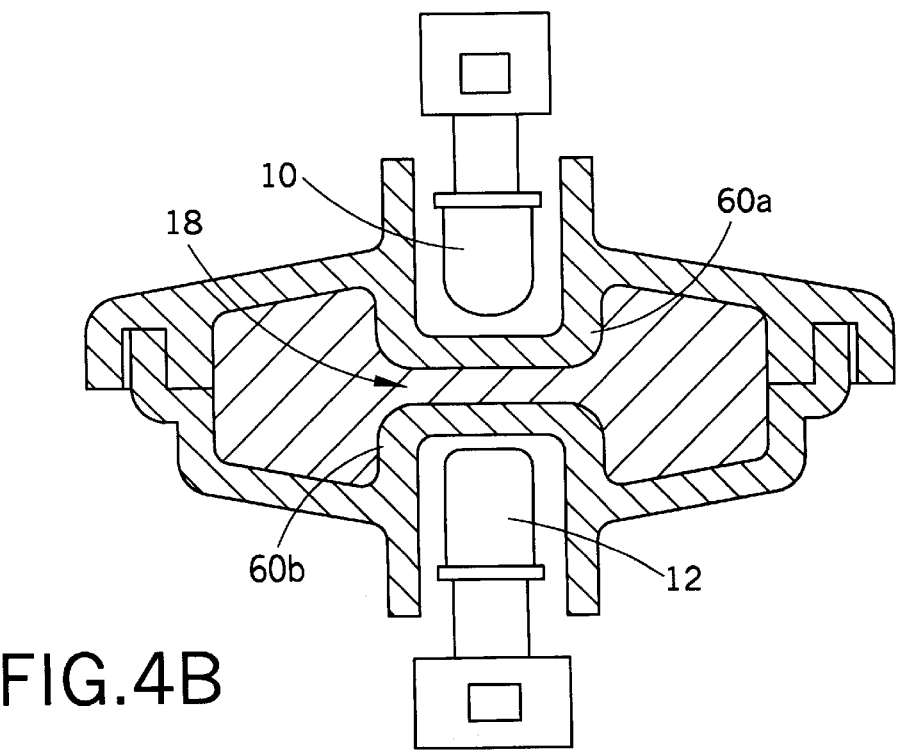
FIG. 4B is a sectional view taken substantially in the direction of arrows 2—2 of FIG. 4A.

Turning attention to FIGS. 4A and 4B, the concentrate sensor arrangement described in connection with FIG. 3 is shown incorporated into a part of flow input 56 and output 58 of FIG. 2. Liquid toner is supplied along toner path 18 towards first opening 62. Dependent upon the luminance of the ink being tested, emitter 10, detector 12 pair is moved substantially in synchronization towards one of first opening 62 or second opening 64. Emitter 10 and detector 12 may, in one embodiment, be mounted to a bracket 72 which is connected to rails 74 thereby allowing the emitter 10, detector 14 pair to move in synchronization when actuated by a motor 76, such as a stepping motor. The locations of emitter 10 and detector 12 are positioned in accordance with signals from controller 78.

It is to be appreciated the movement of the emitter 10, detector 12 pair can be accomplished in other configurations known within the art for simultaneous movement of two elements. It is also considered that the emitter 10 and detector 12 can be moved independently.

Turning attention to FIGS. 5A–5C, a second concentrate sensor D embodiment is illustrated. FIG. 5A shows an end view where variable sensor window 80 is formed as a triangle with a base 82 and an apex 84, where a first window surface 86 touches a section of a second window surface 88. Emitter 10 and detector 12 are provided on the outer surface of sensor window 80. A liquid toner path 90 illustrates that a liquid toner passes through the interior of the triangular area. For a clearer understanding of FIG. 5A, the liquid toner following liquid toner path 90 is flowing into the page through triangular variable concentrate window 80.

FIG. 5B is a side view and FIG. 5C is a top view of FIG. 5A. The apex 84 of concentrate sensor D, allows for an improvement in the sensing of toner. As previously noted, due to the low translucence of black toner, it is necessary to take a very thin sample. The thinnest sample is found at apex 84 where the first window surface 86 and second window surface 88 actually come into contact. Due to mechanical tolerances on existing systems, it is not possible to provide this pinch-point through which liquid toner may travel. Therefore, with black toners which have very low translucence, the present invention provides a useful manner of monitoring an extremely thin layer of low translucent toner, by locating emitter 10, detector 12 pair substantially at apex 84.

Similar to the discussion in connection with FIGS. 3 and 4A-4B, emitter 10, detector 12 are configured to move along the window area from apex 84 to base 82. This allows for an infinitely variable monitoring of toner. Thus, concentrate sensors C and D may be used in systems which have a single monochromatic scheme, existing four color schemes, or future five and six color schemes. Thus, it is not necessary for manufacturers to include additional windows for the added colors, since these colors can be monitored simply by adjusting the location of the emitter 10, detector 12 pair along the surface of sensor window. The emitter 10, detector 12 pair can be moved in a similar manner as described in connection with concentrate sensor C.

Further, during operation of existing devices implementing concentrate sensors C and D, new toner will eventually be needed. An initial operation when new toner is added to a machine is a requirement of calibration. This operation entails moving the liquid toner through the concentrate sensor and pumps until a mixture is consistent. Then the emitter and detector pair measure how much light is passing through, and whether that value is equal to a predetermined acceptable value. For example, if the detected signal is applied as a voltage, it may be known that the certain concentrate level will produce an acceptable value when the output is read as 2 volts, on a 0 volt to 5 volt scale. While in previous systems, a technician would be required to adjust emitter power until a detector voltage of 2 volts was read, under the present invention, emitter 10 will be turned on at one of two extremes, i.e. at opening 64 or apex 84, which would represent 5 volts, or at opening 62 or base 84 of which would read 0 volts. Thereafter, a user will simply move the emitter 10, detector 12 pair until an output of 2 volts is read, setting the system as its operating point.

Also as noted, the tolerances of sensor windows according to the present invention, do not need to be as stringent as is necessary for past devices. This is true since the variability of the emitter 10, detector 12 pair along the variable sensor windows of concentrate sensors C and D can be adjusted to eliminate deficiencies which might exist due to improper tolerances. Specifically, as previously noted due to the infinite variable nature of the present invention, readings can be appropriately calculated by movement of the emitter 10, detector 12 pair to a different location along the variable sensor windows. It is to be appreciated that concentrate sensors C and D may be incorporated in a machine such as shown in FIG. 2.

With respect to the above description, it is to be realized that the optimal dimensional relationships for the parts of the invention, will include variations in size, materials, shape, form, function and manner of operation. Assembly of use are deemed readily apparent and obvious to one skilled in the art and all equivalent relations to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described and accordingly, all suitable modifications and equivalents may be resorted to falling within the scope of the invention.

Having thus described the present invention I now claim:

1. A concentrate sensor for measuring concentration of a material carried in a fluid medium comprising:
    a concentrate sensor window having a first window surface and a second window surface, the first window surface and the second window surface separated from each other and defining therebetween a nonuniform sensor area;
    an emitter positioned to emit light onto the first window surface, through the nonuniform sensor area and out the second window surface;
    a detector positioned to detect the light emitted by the emitter which passes out of the second window surface, and
    a moving means for moving the emitter in a path along the first window surface and the detector in a path along the second window surface, whereby the moving means allows for infinitely positioning of the emitter and the detector along the concentrate sensor window.

2. The concentrate sensor according to claim 1, wherein at least one of the first window surface and the second window surface have a consistently sloping portion which defines the sensor area.

3. The concentrate sensor according to claim 1, wherein the concentrate sensor window is in the configuration of a triangle, wherein at an apex of the triangle a portion of the first window surface and a portion of the second window surface come into contact.

4. The concentrate sensor according to claim 1, wherein the moving means includes a bracket to which the emitter and the detector are attached, such that the emitter and the detector are moved together.

5. The concentrate sensor according to claim 4, wherein the moving means father includes a motor which controls movement of the bracket.

6. The concentrate sensor according to claim 1, wherein the sensor area is configured such that liquid toner ranging from yellow through black can be monitored by the emitter and the detector.

7. The concentrate sensor according to claim 1, wherein the sensor area includes an first opening and a second opening, the first opening being of a larger diameter then the second opening.

8. An electrographic printing device for electrostatically reproducing an image on a recording medium having a dielectric surface, the device comprising:
    a conductive surface, opposite the dielectric surface of the recording medium, configured to be selectively grounded, wherein when a potential difference between the conductive surface and the recording elements is above a threshold level an electrostatic charge is deposited on the dielectric surface of the recording medium;
    a recording station having a plurality of writing electrodes physically positioned on one side of the recording medium to impart selective charges to the recording medium as the recording medium passes the recording station;
    a development station having a fountain of liquid toner concentration, wherein a thin film of the liquid toner is brought into contact with the recording medium and electrostatically attracted to regions of the recording medium to from an image;

a concentrate sensor connected to the development station, including a concentrate sensor window having a first window surface and a second window surface, the first window surface and the second window surface separated from each other and defining therebetween a nonuniform sensor area;

an emitter positioned to emit light onto the first window surface, through the nonuniform sensor area and out the second window surface;

a detector positioned to detect the light emitted by the emitter which passes out of the second window surface, and a moving means for moving the emitter in a path along the first window surface and the detector in a path along the second window surface, whereby the moving means allows for infinitely positioning of the emitter and the detector along the concentrate sensor window.

9. The concentrate sensor according to claim 8, wherein at least one of the first window surface and the second window surface have a consistently sloping portion which defines the sensor area.

10. The concentrate sensor according to claim 8, wherein the concentrate sensor window is in the configuration of a triangle, wherein at an apex of the triangle a portion of the first window surface and a portion of the second window surface come into contact.

11. The concentrate sensor according to claim 8, wherein the moving means includes a bracket to which the emitter and the detector are attached, such that the emitter and the detector are moved together.

12. The concentrate sensor according to claim 11, wherein the moving means father includes a motor which controls movement of the bracket.

13. The concentrate sensor according to claim 8, wherein the sensor area is configured such that liquid toner ranging from yellow through black can be monitored by the emitter and the detector.

14. The concentrate sensor according to claim 8, wherein the sensor area includes an first opening and a second opening, the first opening being of a larger diameter than the second opening.

15. A method for measuring concentration of toner particles carried in a fluid medium in an electrographic printing device, said printing device having a plurality of color toners, the method comprising the steps of:

passing a liquid toner through a nonuniform sensor area, the nonuniform sensor area defined by locations of a first sensor window surface and a second sensor window surface;

sending a signal from an emitter located on the side of the first sensor window surface, through the first window surface, through the nonuniform sensor area, and out the second sensor window;

detecting at least a portion of the signal emitted by the emitter with a detector located on the side of a second sensor window surface; and moving the emitter and the detector along a path of the first and second sensor window surfaces to a location appropriate to detect a concentration level in a liquid toner of a specific color.

16. The method according to claim 15 wherein the step of passing the liquid toner through the nonuniform sensor area includes having the liquid toner pass through a first opening and a second opening, wherein the first opening is of a larger diameter than the second opening.

17. The method according to claim 15 wherein the step of passing the liquid-toner through the nonuniform sensor area which is in the form of a triangle, wherein at least a portion of the first sensor window surface and a portion of the second sensor window surface are in contact at an apex portion and at an opposite end from the apex is a base portion.

18. The method according to claim 17 wherein the step of moving the emitter and detector includes moving the emitter and detector towards the apex portion for a liquid toner which has a low translucence level and moving the emitter and detector towards the base portion for a liquid toner which has a translucence level higher than the liquid toner with the low translucence level.

* * * * *